(12) United States Patent
Akhavan-Tafti et al.

(10) Patent No.: US 7,186,568 B1
(45) Date of Patent: Mar. 6, 2007

(54) ELECTROCHEMILUMINESCENCE FROM ACRIDAN COMPOUNDS

(75) Inventors: Hashem Akhavan-Tafti, Howell, MI (US); Robert Wilson, Willaston (GB); David Jorge Schiffrin, Hoylake (GB)

(73) Assignee: Lumigen Inc., Southfield, MI (US)

( * ) Notice: Subject to any disclaimer, the term of this patent is extended or adjusted under 35 U.S.C. 154(b) by 275 days.

(21) Appl. No.: 10/312,401

(22) PCT Filed: Jun. 26, 2001

(86) PCT No.: PCT/US01/16498

§ 371 (c)(1),
(2), (4) Date: Mar. 31, 2003

(87) PCT Pub. No.: WO02/00726

PCT Pub. Date: Jan. 3, 2002

Related U.S. Application Data

(60) Provisional application No. 60/214,178, filed on Jun. 26, 2000, provisional application No. 60/205,069, filed on Jun. 26, 2000.

(51) Int. Cl.
| | |
|---|---|
| G01N 33/533 | (2006.01) |
| G01N 21/76 | (2006.01) |
| G01N 33/53 | (2006.01) |
| C07K 1/13 | (2006.01) |
| C07D 219/08 | (2006.01) |
| C12Q 1/28 | (2006.01) |

(52) U.S. Cl. .............. 436/546; 436/172; 436/800; 436/805; 435/28; 435/963; 530/405; 546/102

(58) Field of Classification Search ............. 436/544, 436/546, 800, 805, 172; 435/6, 7.1, 26, 28, 435/968, 963; 530/405; 546/102
See application file for complete search history.

(56) References Cited

U.S. PATENT DOCUMENTS

| | | |
|---|---|---|
| 5,491,072 A | 2/1996 | Akhavan-Tafti |
| 5,523,212 A | 6/1996 | Akhavan-Tafti |
| 5,593,845 A | 1/1997 | Akhavan-Tafti |
| 5,670,644 A | 9/1997 | Akhavan-Tafti |
| 5,723,295 A | 3/1998 | Akhavan-Tafti |
| 5,786,141 A | 7/1998 | Bard |
| 5,879,888 A * | 3/1999 | Aizawa et al. .............. 435/6 |
| 5,922,558 A * | 7/1999 | Akhavan-Tafti .............. 435/28 |
| 6,017,769 A * | 1/2000 | Akhavan-Tafti ............. 436/544 |
| 6,030,803 A | 2/2000 | Jacquemijns |
| 6,045,727 A | 4/2000 | Akhavan-Tafti |
| 6,406,913 B1 * | 6/2002 | Ullman et al. .............. 252/700 |

FOREIGN PATENT DOCUMENTS

EP 522677 A1 * 1/1993

OTHER PUBLICATIONS

J.K. Leland;J. Electrochem. Soc., 1990, vol. 137, pp. 3127-3131.
S. Sakura; Anal. Chim. Acta., 1992, vol. 262, pp. 49-57.
R. Wilson; Biosensors & Bioelectronics, 1997, vol. 12, pp. 277-286.
R. Wilson; J.of Electroanalytical Chemistry, 1998, vol. 448, pp. 125-130.
J.S.Littig; Analytical Chemistry, 1992, vol. 64, pp. 1104-1144.
H. Akhavan-Tafti; J. Org. Chem., 1998, vol. 63, pp. 930-937.
H. Akhavan-Tafti; Clin. Chem.,1995, vol. 41, No. 9, pp. 1368-1369.
P. Hapiot; J. Am. Chem. Soc., 1990, vol. 112, pp. 1337-1343.
G.M. Greenway; Trends in Analytical Chemistry,1990, vol. 9, pp. 200-203.
A.W. Knight; Analyst, 1994, vol. 119, pp. 879-890.
A.W. Knight; Trac. Trends Anal. Chem., 1999, vol. 18, pp. 47-62.
D.R. Deaver; Nature, 1995, vol. 377, pp. 758-760.
G.F. Blackburn, Clinical Chemistry, 1991, vol. 37, pp. 1534-1539.
D.L. Gatto-Menking; Biosensors & Bioelectronics, 1995, vol. 10, pp. 501-507.
H.Yu; J. Immunol. Methods, 1996, vol. 192, pp. 63-71.
S. Zhao; BioTechniques, 1996, vol. 21, pp. 726-731.
C. O'Connell, Clinical Chemistry, 1998, vol. 44, pp. 1161-1169.

* cited by examiner

*Primary Examiner*—Long V. Le
*Assistant Examiner*—Shafiqul Haq
(74) *Attorney, Agent, or Firm*—Richard S. Handley

(57) ABSTRACT

Methods are disclosed for producing electrochemiluminescence by electrochemically oxidizing an acridan compound at an electrode in the presence of a peroxide. Maintaining a sufficiently positive potential results in continuous oxidation of the acridan compound to an acridinium compound which reacts with peroxide to produce the luminescence. Light emission can be reversibly and repeatedly cycled on and off by sweeping the potential between two values. The acridan compounds can be provided with a labeling group for linking to an analyte or analyte binding partner. The present electrochemiluminescent reaction can find use in assay methods for detecting analytes by immunoassays and nucleic acid assays.

22 Claims, 7 Drawing Sheets

Plan View

Front Elevation - Section On Centre Line

ELECTROCHEMILUMINESCENCE FROM ACRIDAN COMPOUNDS

CROSS REFERENCE TO RELATED APPLICATION

The present application resulted from National Stage Entry of PCT Application US01/16498 filed on Jun. 26, 2001 which claims the benefit of Provisional Application No. 60/205,069, filed on Jun. 26, 2000.

This application claims priority from Provisional U.S. Application No. 60/214,178, filed Jun. 26, 2000.

FIELD OF THE INVENTION

The present invention relates to the field of electrochemiluminescence which is the production of luminescence by an electrochemical reaction. In particular the present invention relates to methods of producing electrochemiluminescence from acridan compounds. The present electrochemiluminescent reaction can find use in assay methods for detecting analytes. The acridan compounds can be provided with a labeling group for linking to an analyte or analyte binding partner.

BACKGROUND OF THE INVENTION

Electrochemiluminescence (ECL) has received widespread attention during the previous decade, especially in the field of chemical analysis. It combines the well known sensitivity of chemiluminescence (CL) with the precise control over the time and position of light emitting reactions afforded by electrochemistry. As an alternative approach for conducting immunoassays and nucleotide assays it offers advantages such as increased sensitivity and precision, reduction in time and labor, and the elimination of radioisotopes. In order to exploit the full potential of this technology there is a requirement for new chemiluminescent compounds which can be initiated electrochemically. We show for the first time how CL can be triggered by electrochemical oxidation of acridan compounds.

Prior to the present invention, ruthenium chelates and luminol derivatives were the only compounds that have been used in a significant number of analytical applications involving ECL. (J. K. Leland and M. J. Powell, J. Electrochem. Soc., 1990, 137, 3127; S. Sakura, Anal. Chim. Acta., 1992, 262, 49) Ruthenium chelates have been used for enzyme assays, but their most significant impact has been as labels for immunoassays and nucleotide assays. In these applications a combination of ECL and magnetic bead technology has found increasing use in pharmaceutical labs for high throughput screening. Luminol has also been used for enzyme assays and immunoassays. Light is emitted when electrochemically oxidized luminol reacts with hydrogen peroxide which allows the reaction to be coupled to oxidase enzymes such as glucose oxidase. (R. Wilson and A. P. F. Turner, Biosensors, 1997, 12, 277) The chemiluminescence reaction of luminol is also catalyzed by electrochemically oxidized ferrocenes (R. Wilson and D. J. Schiffrin, J. Electroanal. Chem., 1998, 448, 125) suggesting that these compounds could be used as labels in an ECL system resembling the one based on ruthenium chelates.

Acridinium esters were discovered in 1964 and subsequently developed as labels for immunoassays and nucleotide assays. The chemiluminescence reaction mechanism of these compounds involves nucleophilic attack of a peroxide anion (HOO—) in alkaline solution on the 9-position of the acridinium nucleus followed by internal cyclization leading to the formation of a metastable dioxetanone intermediate. This spontaneously decarboxylates to give the singlet excited state of N-methylacridone, which emits blue light at 430 nm when it relaxes to the ground state. The chemiluminescence quantum yield is typically between 1 and 10%. The reaction is extremely rapid, but in the absence of peroxide other nucleophiles such as hydroxide ion can form an adduct (pseudo-base) with the 9-position of the acridinium nucleus. Formation of this intermediate precludes the formation of a dioxetanone intermediate and therefore no light is emitted unless pseudo-base formation is reversed by an acidic solution of hydrogen peroxide before adding a sodium hydroxide solution.

Electrochemical triggering of the chemiluminescent reaction of an acridinium ester at a pH of 5.0 was developed in an attempt to simplify the conventional initiation procedure. (J. S. Littig and T. A. Neeman, Anal. Chem., 1992, 64, 1140–1144) This pH is not particularly useful for immunoassays and nucleotide assays. A solution of acridinium ester was injected into a flowing stream of pH 12 phosphate buffer and pumped into a flow cell. Chemiluminescence was triggered in the cell by reducing dissolved oxygen electrochemically. The conditions are a compromise between those required for chemiluminescence and oxygen reduction, and those necessary to avoid pseudo-base formation. It would also be necessary to control the concentration of dissolved oxygen to obtain precise results which cancels out the increase in simplicity obtained by initiating the chemiluminescent reaction electrochemically. These drawbacks are avoided when an acridan ester is used because the acridinium ester is produced in situ from a passive precursor.

Recently a large number of acridans (reduced acridinium esters, thioesters and amides) based on the N-alkylacridancarboxylate nucleus, including DMC, have been made. (H. Akhavan-Tafti, et al., J. Org. Chem. 1998, 63, 930–937; H. Akhavan-Tafti et al., Clin. Chem. 1995, 41, 1368–1369) These acridan compounds are stable in the presence of hydrogen peroxide and do not form an inactive pseudo-base. Light emission can be triggered by enzymatically oxidizing the acridan with the enzyme horseradish peroxidase (HRP) in the presence of hydrogen peroxide and an enhancer such as p-iodophenol. HRP oxidizes the acridan to the corresponding acridinium ester, which in most cases is immediately subject to nucleophilic attack by the peroxide anion (HOO—) at the 9 position of the acridinium nucleus; the possibility of pseudo-base formation does not arise because peroxide is several orders of magnitude more nucleophilic than hydroxide. Nucleophilic attack on the acridinium ester results in the formation of a dioxetanone which decomposes to form the singlet excited state of N-methylacridone. This in turn relaxes to the ground state accompanied by the emission of intense blue light with a maximum wavelength of 430 nm. By using these compounds as a substrate for HRP it has been possible to detect as little as 0.1 amol of this enzyme in a 15 minute assay.

Previous work on the electrochemistry of acridan which does not bear a carbonyl group at the 9-position demonstrated the oxidation by a mechanism in which the second oxidation step occurs in solution as a result of disproportionation between protonated and unprotonated radical intermediates. (P. Hapiot, J. Moiroux and J. M. Saveant, J. Am. Chem. Soc., 1990, 112, 1337) This reaction did not involve the production of chemiluminescence.

Acridan compounds substituted with an oxidizable exocyclic double bond are disclosed in commonly assigned U.S. Pat. No. 5,922,558. These compounds are enzymatically oxidized by a peroxidase enzyme to produce visible light. The opposite terminus of the double bond bears two substituents, one being an ether or thioether-type group, the other being any of various groups such as ether or thioether-type groups, alkoxy, aryloxy, alkylthio, arylthio, trialkylsilyloxy, phosphoryloxy, acyloxy and acylthio groups. Compounds of this type having a phosphate salt group are also disclosed in commonly assigned U.S. Pat. No. 6,045,727 which describes their enzymatic reaction with phosphatase enzymes to produce chemiluminescence.

SUMMARY OF THE INVENTION

It is an object of the present invention to provide a method for producing chemiluminescence by an electrochemical reaction. It is a further object of the present invention to provide a method for producing chemiluminescence by the electrochemical reaction of acridan compounds in the presence of a peroxide, particularly hydrogen peroxide. A further object of the invention is to provide a method for conducting an assay of an analyte using an electrochemiluminescent reaction to produce light for detecting the analyte.

GENERAL DESCRIPTION

The present invention concerns the electrochemiluminescent oxidation of acridan derivatives. We have found that the electrochemical oxidation of acridan compounds in the presence of peroxide at neutral to alkaline pH results in the generation of visible luminescence above a certain minimum potential. The reaction adds to the small number of analytically useful electroluminescent reactions and can find use in assay methods for detecting analytes. For example, the acridan compound can be provided with a labeling group for linking to an analyte or analyte binding partner.

A first group of acridan compounds useful in the practice of the present invention comprise acridan-carboxylic acid derivatives having the general formula:

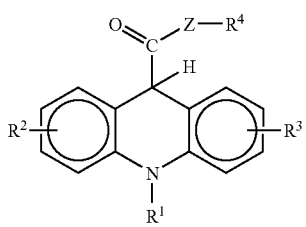

wherein $R^1$ to $R^4$ can be any of a variety of groups provided that they do not interfere with the production of chemiluminescence. The Z group is O, S, or NR wherein R can be any of a variety of groups but is preferably a sulfonyl group.

Unlike art-known methods of generating luminescence electrochemically using an acridinium ester, the reaction does not involve the electrochemical generation of $H_2O_2$ or superoxide. The acridan compounds used in the present methods are significantly more stable that the corresponding acridinium compounds and should provide more robust labels.

The electrochemiluminescence is generated by subjecting a solution of the acridan compound and peroxide to a positive potential above a certain threshold. The threshold value is easily determined by voltammetric scan or by measuring luminescence during a voltage sweep as described below.

A second group of acridan compounds useful in the practice of the present invention comprise compounds having the general formula:

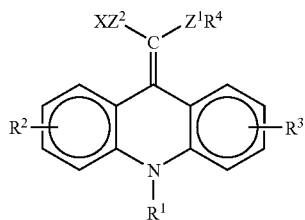

wherein $Z^1$ and $Z^2$ are independently selected from O, S and NR atoms wherein R can be any of a variety of groups but is preferably a sulfonyl group, and wherein $R^1$ to $R^4$ and X can be any of a variety of groups provided that they do not interfere with the production of chemiluminescence.

DETAILED DESCRIPTION OF THE INVENTION

Figure 1:
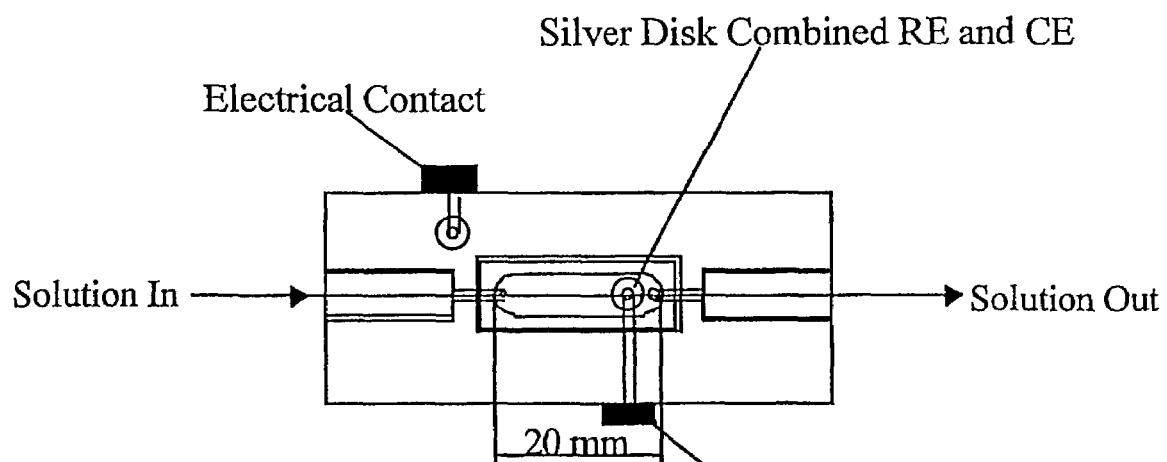
FIG. 1 depicts a laminar flow cell used for electrochemiluminescence detection of acridans.
Figure 1:
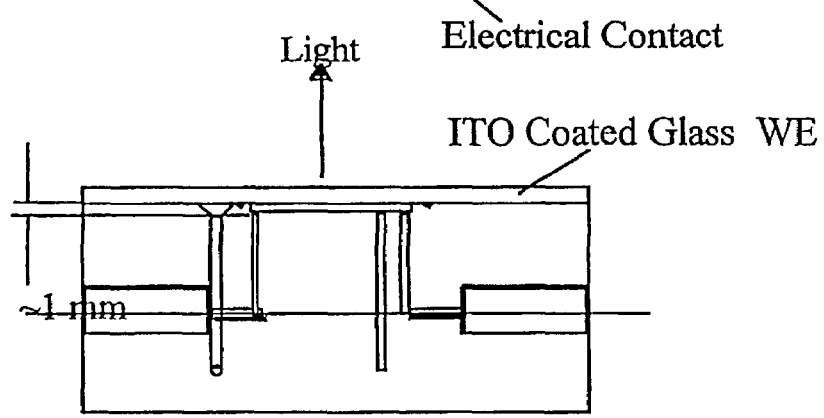

We now show for the first time that chemiluminescence (CL) of certain acridan compounds can be triggered by electrochemical oxidation in the presence of hydrogen peroxide. Subjecting the acridan compound to an appropriate potential at the anode of an electrochemical cell containing a solution of the acridan compound and a peroxide such as $H_2O_2$ results in the production of visible light which persists for an extended time if as the potential is maintained at an appropriate value. Reversing the potential leads to a rapid extinction of light emission. The process can be repeatedly cycled to reversibly turn light emission on and off until either the acridan or the peroxide is depleted.

Chemiluminescence is the emission of light by the electronically excited product of a chemical reaction when it relaxes to the ground state. The efficiency of a chemiluminescent reaction is given by the quantum yield ($\Phi_{CL}$), which is a measure of the fraction of reacting molecules that actually produce light. For analytical chemists the main attraction of CL is the opportunity to carry out sensitive assays over a wide range of concentrations using relatively inexpensive equipment. In practice it is usually combined with a complementary technique that confers specificity on the CL reaction. The most widely used example of such a technique is immunoassay where CL labels such as acridinium esters have been used to detect analytes at picomolar concentrations. By developing CL compounds which can be used as substrates for the enzyme labels it is possible to increase the speed of CL immunoassays without impairing the sensitivity.

Electrochemiluminescence (ECL) is a form of CL in which the chemiluminescent reaction is preceded by an electrochemical reaction. (Greenway, G. M. Trends Anal. Chem. 1990, 9, 200–203; Knight, A. W.; Greenway, G. M. Analyst, 1994, 119, 879–890; Knight, A. W. Trac Trends Anal. Chem., 1999, 18, 47–62.) The advantages of CL are retained, and electrochemistry allows the time and position of the light emitting reaction to be controlled. By controlling the time of the reaction light emission can be delayed until events such as an immune or enzyme catalyzed reaction have taken place. Although similar control can be exercised over alternative detection methods such as fluorescence the equipment is considerably more sophisticated and expensive. Control over position can be used to confine light emission to a region which is precisely located with respect to the detector, improving sensitivity by increasing the ratio of signal to noise. A good example of this is the combination of ECL with magnetic bead technology, which allows bound label to be distinguished from unbound label without a separation step as disclosed in Deaver, D. R. Nature, 1995, 377, 758–760; and Blackburn, G. F., et al. Clin. Chem. 1991, 37, 1534–1539. Control over position could also be used to determine the results of more than one analytical reaction in the same sample by interrogating each electrode in an array, either in sequence, or simultaneously using a position sensitive detector.

2',6'-Difluorophenyl 10-methylacridan-9-carboxylate (DMC) and 2',3',6'-trifluorophenyl 10-methylacridan-9-carboxylate (PS-3) belong to a class of acridancarboxylic acid derivatives that undergo a chemiluminescent reaction with peroxidase enzymes in the presence of a peroxide. Exemplary compounds are disclosed in U.S. Pat. Nos. 5,491,072, 5,523,212, 5,593,845, 5,670,644, 5,723,395, and 6,030,803. These patents describe methods of preparing suitable acridan compounds. A first group of acridan compounds useful in the practice of the present invention comprise acridancarboxylic acid derivatives having the formula:

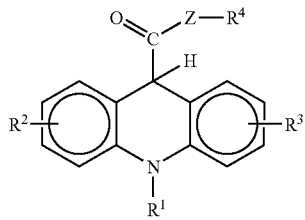

wherein $R^1$ to $R^4$ are independently selected from hydrogen and organic groups containing from 1 to 50 non-hydrogen atoms selected from C, N, O, S, P and halogen atoms which do not interfere with the production of chemiluminescence, wherein at least one of the groups $R^1$–$R^4$ can be a labeling substituent of the formula

-L-RG

L is a linking group which can be a bond or another divalent or polyvalent group, RG is a reactive group which enables the chemiluminescent labeling compound to be bound to another compound, Z is selected from O, S and $NR^5$, $R^5$ is selected from substituted or unsubstituted alkyl, substituted or unsubstituted aryl, alkylsulfonyl and arylsulfonyl groups. Representative organic groups for $R^1$ to $R^4$ include, without limitation, alkyl, alkyl, aryl, aryl, alkenyl, alkynyl or aralkyl any of which can be substituted, halogen, hydroxy, alkoxy, amino, alkylamino, carbonyl-containing groups such as keto, carboxy, carboxamide and carboalkoxy, thio, alkylthio, cyano, nitro, trialkyl-silyloxy, alkylsulfonyl, arylsulfonyl, and positively or negatively charged ionic groups which improve water solubility. The acridan ring can be substituted with from 0 to 8 substituents other than hydrogen, these are designated $R^2$ and $R^3$.

The linking group L can be a bond, an atom, or a straight, or branched chain of atoms some of which can be part of a ring structure. The substituent usually contains from 1 to about 50 non-hydrogen atoms, more usually from 1 to about 30 non-hydrogen atoms. Atoms comprising the chain are selected from C, O, N, S, P, Si, B, and Se atoms, preferably from C, O, N, P and S atoms. Halogen atoms can be present as substituents on the chain or ring. Typical functional groups comprising the linking substituent include alkylene, arylene, alkenylene, ether, peroxide, carbonyl as a ketone, ester, carbonate ester, thioester, or amide group, amine, amidine, carbamate, urea, imine, imide, imidate, carbodiimide, hydrazine, diazo, phosphodiester, phosphotriester, phosphonate ester, thioether, disulfide, sulfoxide, sulfone, sulfonate ester, sulfate ester, and thiourea groups.

The reactive group RG is an atom or group whose presence facilitates bonding to another molecule by covalent attachment or physical forces. In some embodiments, attachment of a chemiluminescent labeling compound of the present invention to another compound will involve loss of one or more atoms from the reactive group for example when the reactive group is a leaving group such as a halogen atom or a tosylate group and the chemiluminescent labeling compound is covalently attached to another compound by a nucleophilic displacement reaction. In other embodiments, attachment of a chemiluminescent labeling compound to another compound by covalent bond formation will involve reorganization of bonds within the reactive group as occurs in an addition reaction such as a Michael addition or when the reactive group is an isocyanate or isothiocyanate group. In still other embodiments, attachment will not involve covalent bond formation, but rather physical forces in which case the reactive group remains unaltered. By physical forces is meant attractive forces such as hydrogen bonding, electrostatic or ionic attraction, hydrophobic attraction such as base stacking, and specific affinity interactions such as biotin-streptavidin, antigen-antibody and nucleotide-nucleotide interactions.

Numerous acridan compounds have been found to exhibit electrochemiluminescence at positive potentials (relative to Ag/AgCl) in the presence of peroxide. Examples include:

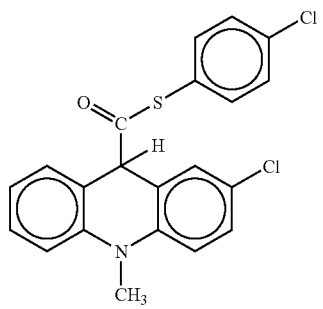
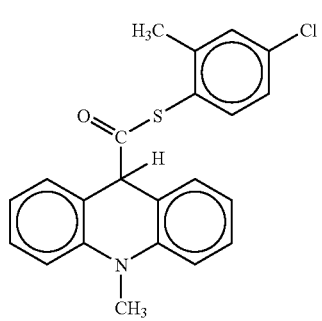
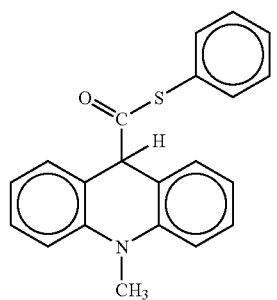
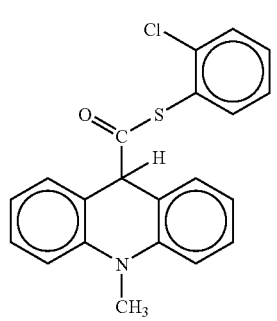
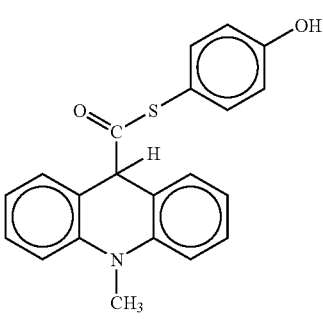
-continued
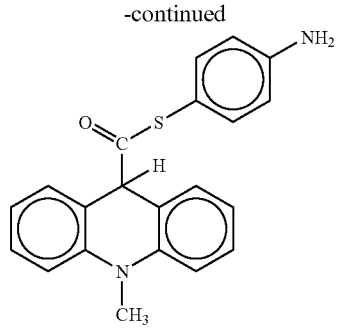
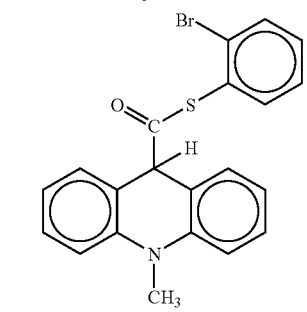
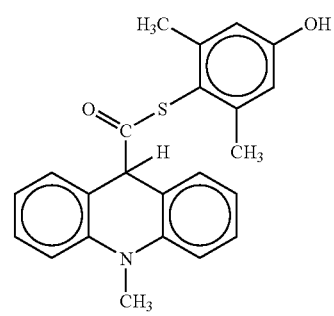
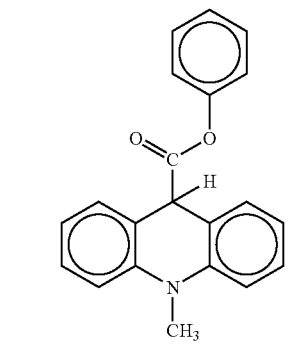
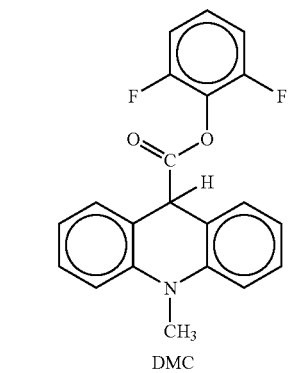
DMC -continued
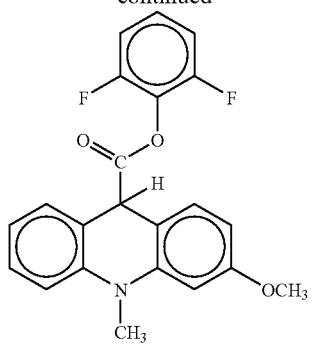
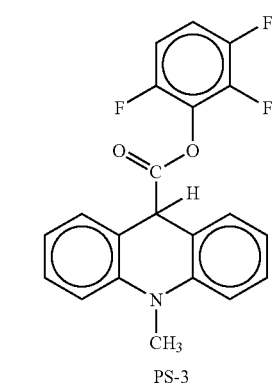
PS-3
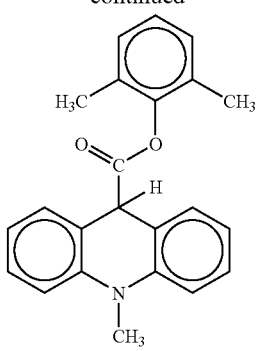
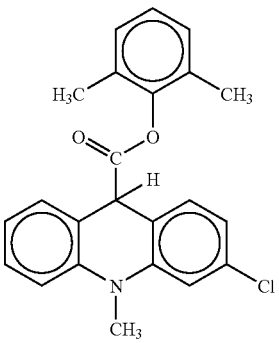
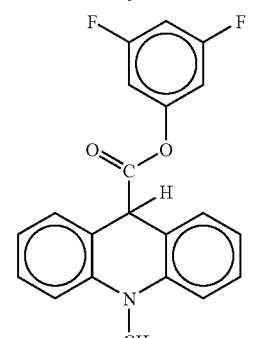
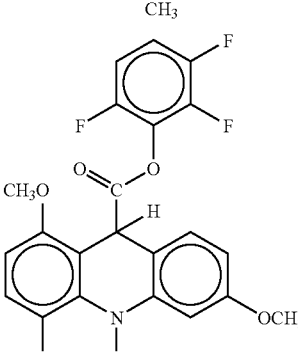
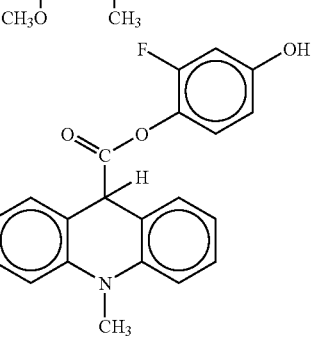

-continued

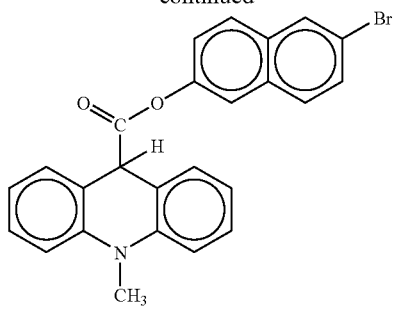

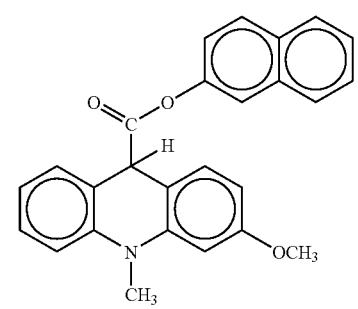

A second group of acridan compounds useful in the present electrochemiluminescent methods comprise a group of acridan compounds bearing an exocyclic double bond at the 9-position and having the formula:

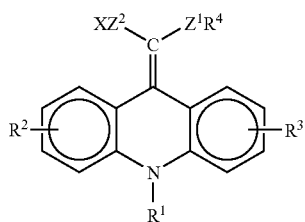

wherein $Z^1$ and $Z^2$ are independently selected from O, S and $NR^5$, $R^5$ is selected from substituted or unsubstituted alkyl, substituted or unsubstituted aryl, alkylsulfonyl and arylsulfonyl groups, and wherein $R^1$ to $R^4$ are as defined previously. The group X is selected from hydrogen and organic groups containing from 1 to 50 non-hydrogen atoms selected from C, N, O, S, P and halogen atoms which do not interfere with the production of chemiluminescence preferably an alkyl, aryl, aralkyl, alkenyl or alkynyl group of 1–20 carbon atoms any of which can be substituted, or is selected from substituted or unsubstituted alkyl or aryl carbonyl groups having from 1–20 carbon atoms, tri($C_1$–$C_8$ alkyl)silyl groups, an $SO_3^-$ group, glycosyl groups and phosphoryl groups of the formula PO(OR')(OR") wherein R' and R" are independently selected from substituted or unsubstituted alkyl, substituted or unsubstituted aryl and substituted or unsubstituted aralkyl groups of 1–20 carbon atoms, trialkylsilyl groups, alkali metal cations, alkaline earth cations, ammonium and phosphonium cations. Substituted alkyl groups will contain at least one group other than a hydrogen atom, such as ionic groups or polar groups. The group X can optionally comprise a group -L-RG as defined above.

A preferred set of compounds of this type has a phosphate group for the group $Z^2X^2$ and are depicted by the formula

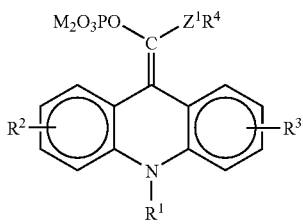

wherein M is a cation, preferably an alkali metal ion or an ammonium, quaternary ammonium or quaternary phosphonium ion. Another group of compounds has an ester group and is depicted by the formula:

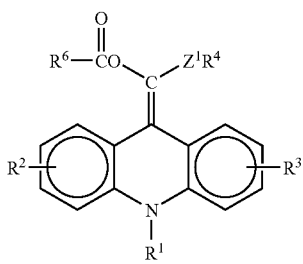

wherein $Z^1$ and $R_1$–$R^4$ are as defined previously and $R^6$ is an alkyl or aryl group which can be further substituted.

Numerous acridan compounds of this type have been found to exhibit electrochemiluminescence at positive potentials (relative to Ag/AgCl) in the presence of peroxide. Examples include the compounds below.

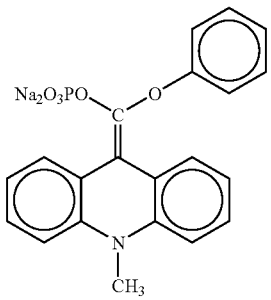

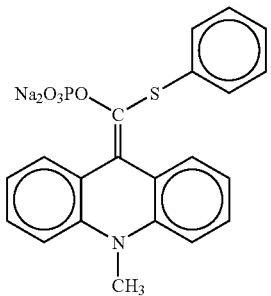

APS-2

-continued

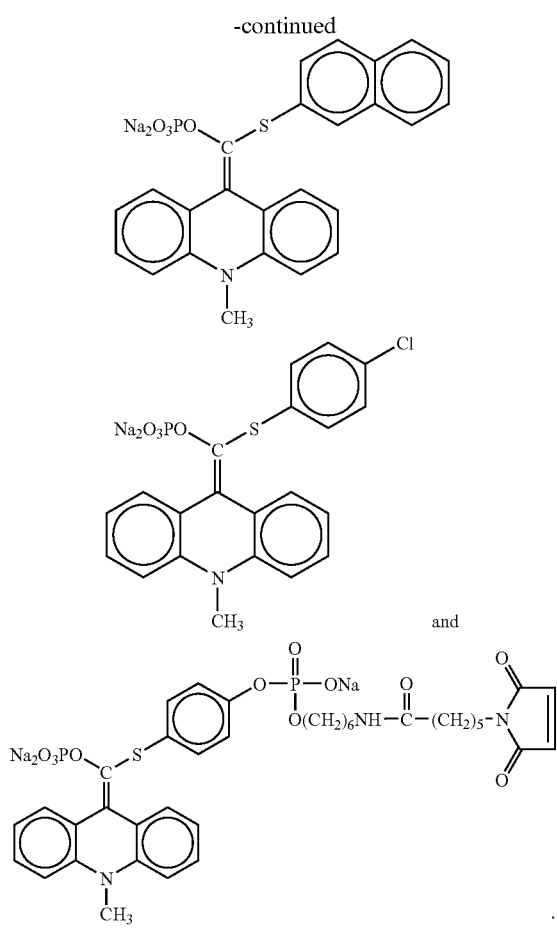

and

Suitable instrumentation for performing the electrochemical and luminescent measurements are disclosed in the Deaver and Blackburn references described above, in U.S. Pat. No. 5,786,141 and by reference to the examples described in detail below. An apparatus useful in performing the methods of the present invention is depicted in FIG. 1. Various types of electrode materials as are known in the electrochemical arts can be used including graphite rods, platinum wires or mesh. The physical shape, size and configuration can be determined at the convenience of the user and is not meant to limit the nature of the invention. Transparent indium tin oxide (ITO) electrodes are attractive for use in electrochemiluminescence (ECL) because the intensity of light emitted at the interface between the electrode and the solution can be determined by placing a detector behind the electrode. This avoids interference from absorbing molecules in solution. ITO has been used as an electrode on many occasions. It has a large optical band-gap and therefore it is transparent to light in the visible region of the electromagnetic spectrum. This makes it attractive for ECL work because light emitted at the ITO surface can be transmitted through the electrode to the detector without interference from absorbing molecules in solution. Against these advantages must be weighed the limitations imposed by the corrosive effect of anodic potentials in excess of 1 V, and of the electroluminescence observed when hydrogen peroxide is oxidized (or reduced). The corrosive effect of anodic potentials due to an increase in tin oxide at the surface of the electrode leads to loss of conductivity. Anodic electroluminescence was a source of background noise in acridan and luminol ECL, which led to a decrease in sensitivity.

The electrochemical and chemiluminescence properties of DMC and PS-3 have been studied in detail, but it should be understood that a large number of related acridans are suitable for electrochemiluminescence assays. Acridans are stable in solid form with no detectable change in chemiluminescent activity at ambient temperature for more than two years provided light is excluded. DMC was stable in PBS for 8 hours and, unlike the corresponding acridinium ester, it is not prone to pseudo-base formation. Therefore labels would remain active during the period when antibody or nucleotide binding reactions were taking place. At the end of this time the sample would be pumped into a flow cell where acridan label bound to a solid phase in suspension would be separated from the rest of the sample and concentrated on an electrode. Then the flow cell would be filled with buffered hydrogen peroxide solution containing EDTA to curtail trace metal ion contaminant catalyzed oxidation of the acridan, and a non-ionic detergent (Tween-20) to enhance light emission.

Cyclic voltammetry and linear sweep voltammetry with luminometric detection were carried out with a Ag/AgCl reference electrode. In a typical experiment the concentration of DMC and the corresponding acridinium ester was 50 µM and 5 µM respectively. The second cyclic voltammogram (CV) of DMC shown in FIG. 2 has three peaks located at 0.76 V (peak A), −0.25 (peak B) and −0.11 V (peak C). A plot of light intensity at 430 nm against applied potential for DMC in the presence of hydrogen peroxide (FIG. 3) has a single peak at 0.75 V corresponding to the position of peak A in FIG. 2.

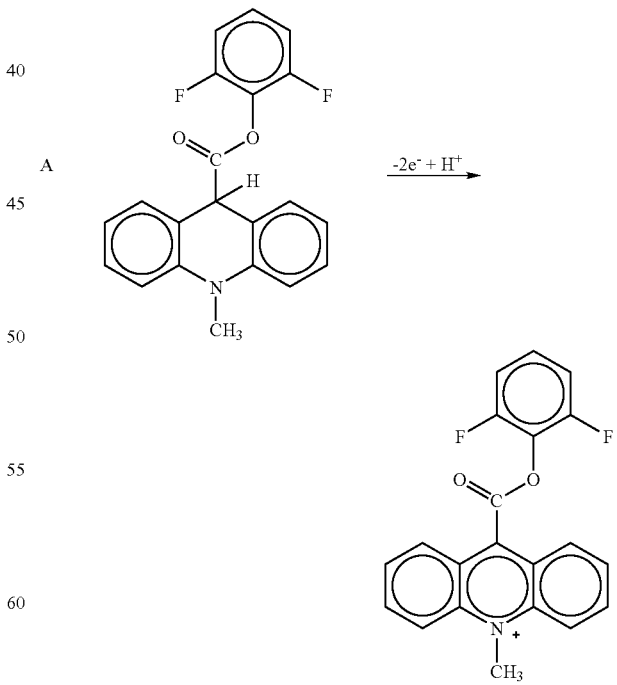

This suggests that peak A represents the two electron oxidation of DMC to the corresponding acridinium ester as shown above. The acridinium ester then reacts with hydrogen peroxide to generate chemiluminescence as shown below.

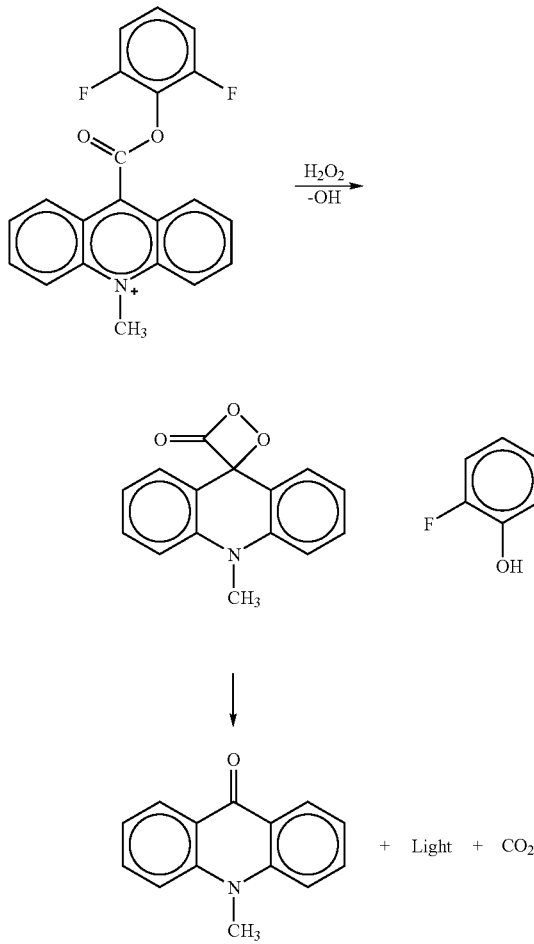

Figure 2:
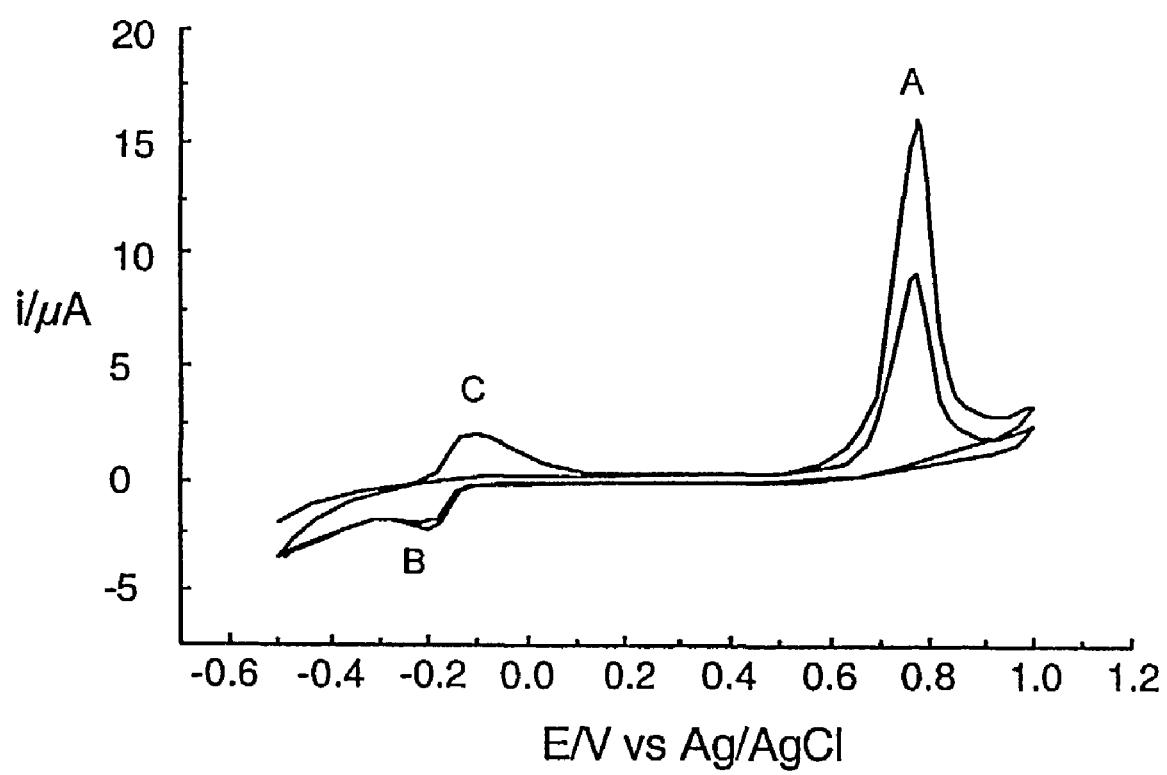
FIG. 2 depicts two successive cyclic voltammograms of 50 µM DMC in 10 mM Tris buffer with 0.1 M NaCl, 10 mM hydrogen peroxide, and 0.025% Tween-20. Scan rate 100 mV/s, the 1st scan contains peaks A and B; the 2nd scan contains peaks A, B and C.
Figure 3:
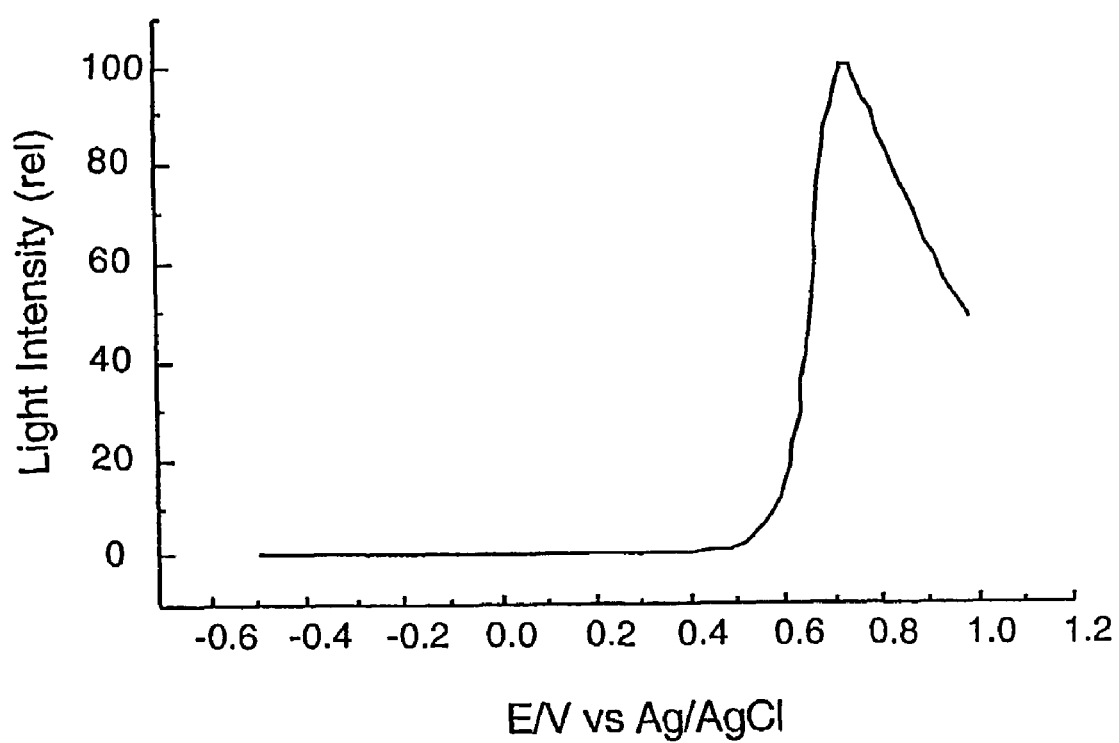
FIG. 3 is a graph showing the dependence of electrochemiluminescence on potential for 50 µM DMC at pH 8.0, in 10 mM Tris buffer with 0.1 M NaCl, 10 mM hydrogen peroxide, 1 mM EDTA and 0.025% Tween-20 at a scan rate 10 mV/s.

Peaks B and C in FIG. 2 only appear in the CV after oxidation of DMC and therefore peak B must represent the reduction of an oxidation product. Light emission in the presence of hydrogen peroxide indicates that an acridinium ester is produced when DMC is oxidized and the simplest explanation for peak B is that it represents reduction of this product as shown below.

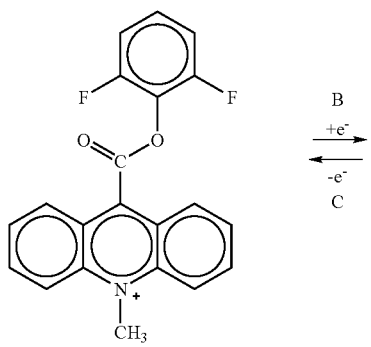

-continued

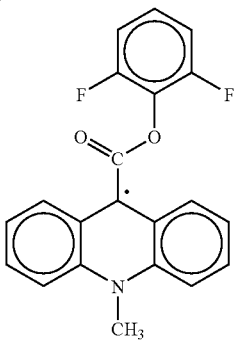

This is supported by the observation that peak B is almost absent when a CV is obtained in the presence of hydrogen peroxide, as would be expected if the compound responsible reacts with peroxide. Further investigation of this hypothesis with an authentic sample of the acridinium ester corresponding to DMC gave a CV with two peaks identical to B and C in FIG. 2.

Enzymatic oxidation of DMC by HRP has been reported to occur in two one-electron oxidation steps separated by a non-enzymatic deprotonation. The corresponding electrochemical pathway would be a classic ECE mechanism in which the two enzymatic steps are replaced by electrochemical oxidations. Previous work on acridans, however, has suggested an alternative mechanism in which the second oxidation step occurs in solution as a result of disproportionation between protonated and unprotonated radical intermediates. (Hapiot, et al., ibid.) Further work is required to reveal which mechanism applies to DMC.

Figure 5:
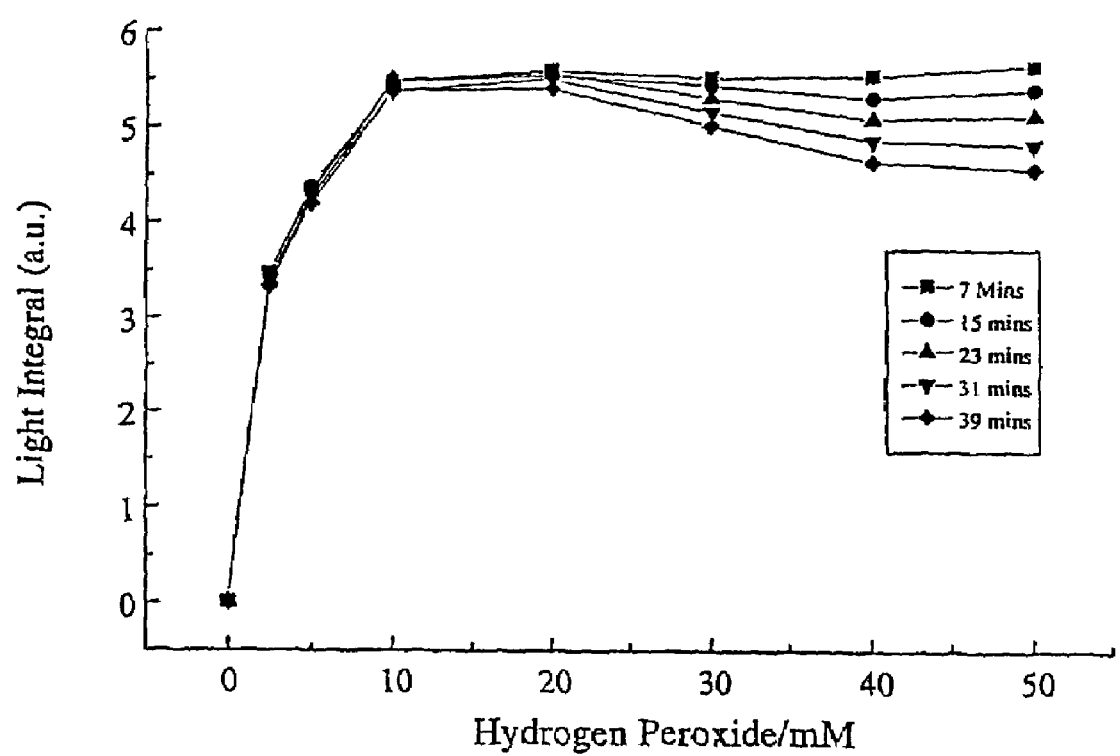
FIG. 5. Dependence of electrochemiluminescence on hydrogen peroxide concentration for 10 nM DMC at pH 8.0, in 10 mM Tris buffer with 0.1 M NaCl, 1 mM EDTA and 0.025% Tween-20. Five measurements, at 7 minute intervals, were made at each concentration by integrating the light intensity for 30 s after a potential step from 0 to 1 V.
Figure 6:
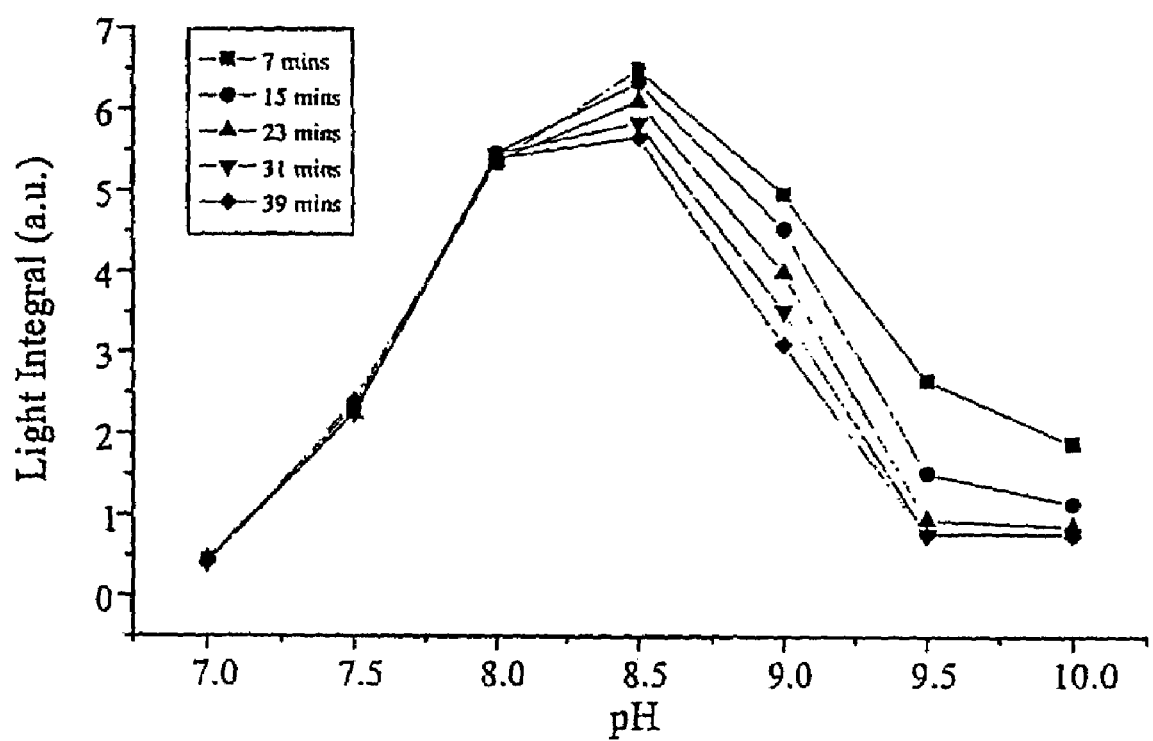
FIG. 6. Dependence of electrochemiluminescence on pH for 10 nM DMC in 10 mM Tris/AMP buffer with 0.1 M NaCl, 10 mM hydrogen peroxide, 1 mM EDTA and 0.025% Tween-20. Five measurements, at 7 minute intervals, were made at each concentration by integrating the light intensity for 30 s after a potential step from 0 to 1 V.
Figure 7:
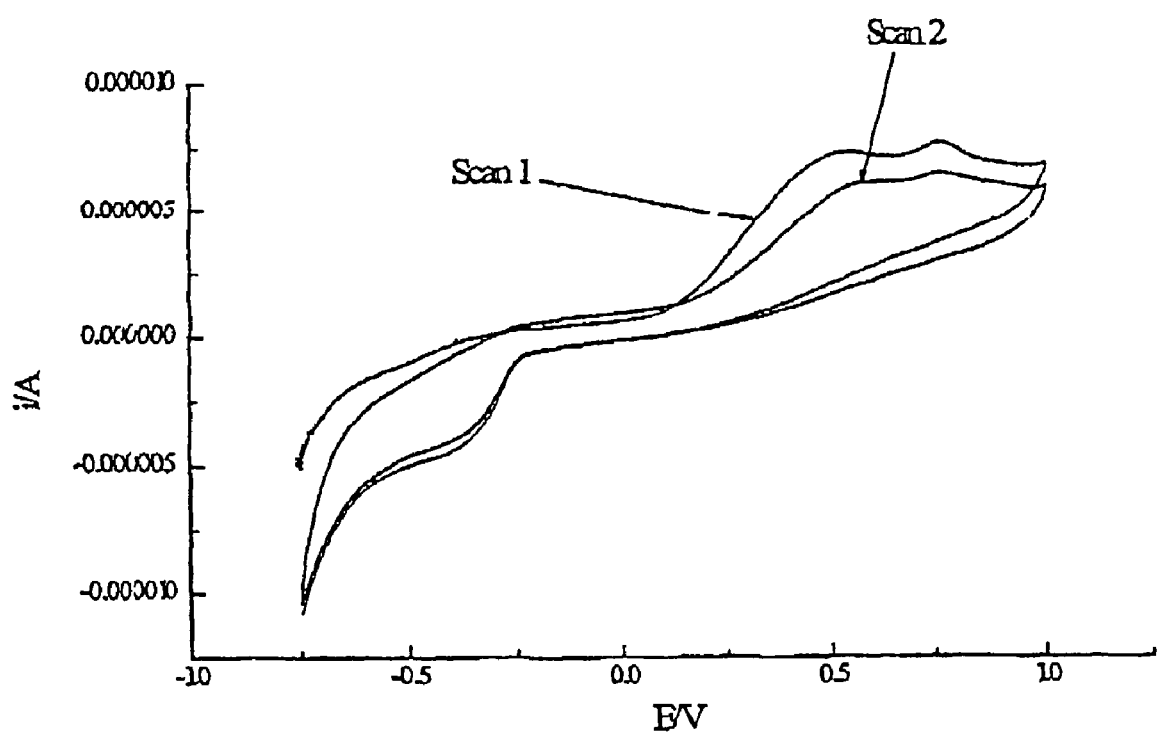
FIG. 7 depicts two successive cyclic voltammograms of APS-2 in 1 with hydrogen peroxide. Scan rate 10 mV/s.

Investigation of the effect that pH (FIG. 5) and hydrogen peroxide concentration (FIG. 6) had on the electrochemiluminescence of DMC showed that it was stable at pH 8.0 in the presence of 10 mM hydrogen peroxide for at least 40 minutes. This was considerably longer than the time required to fill the flow cell with solution and even exceeds the time required for most binding reactions, suggesting that it would be possible to carry out separation free assays provided other reagents and the analyte are unaffected by 10 mM hydrogen peroxide. The pH of the electrochemiluminescence solution (8.0) is close to that at which binding reactions would be carried out (typically 7.5) and therefore dissociation of bound antibodies or nucleotide duplexes would be unlikely to occur while the flow cell was being filled. A plot of the integrated light intensity against concentration for DMC in the range in 0 to 10 nM was linear. The limit of detection, calculated as the concentration equivalent to mean+2.5×SD of the zero calibrator (n=9), was 54 pM. This figure meets the requirements of many analytical reactions which are carried out using immunoassays even without prior concentration of the acridan on an electrode. It compares favorably with the lower limit of 100 pM reported for luminol electrochemiluminescence, and is close enough to the 0.2 pM detection limit reported for ruthenium chelates to suggest that related acridans, which produce more intense electrochemiluminescence, are practical alternatives to existing labels.

The ECL of another acridan ester 2',3',6'-difluoro-phenyl 10-methylacridan-9-carboxylate (PS-3), and luminol were measured using ITO electrodes. The electrochemistry and ECL of all compounds was studied by cyclic voltammetry and linear sweep voltammetry with luminometric detection.

Electrochemical oxidation of the acridan ester converts it to the corresponding acridinium ester, which undergoes chemiluminescent reaction with $H_2O_2$. Electrochemical oxidation of luminol also yields a product that undergoes chemiluminescent reaction with $H_2O_2$. The effects of pH and $H_2O_2$ concentration on acridan ester and luminol ECL were investigated in a planar flow cell. The acridan ester was stable for at least 40 minutes at pH 8.0 in the presence of $H_2O_2$. The limits of detection of the acridan ester and luminol under these conditions were 65 pm and 72 pM respectively.

Assays

Although electrochemiluminescence reactions have been known for many years, efforts to exploit their potential as an analytical technique have only been begun recently. To date the most successful development is a combination of ECL and paramagnetic bead technology which has made it possible to carry out high throughput immunoassays (Gatto-Menking, D. L., Yu, H., Bruno, J. G., Goode, M. T., Miller, M., Zulich, A. W. Biosensors and Bioelectronics 1995, 10, 501–507; Yu, H. J. Immunol. Methods 1996, 192, 163–171) and nucleotide assays. (Zhao, S., Consoli, U., Arceci, R., Pfeifer, J., Dalton, W. S.;, Andreeff, M. BioTechniques 1996, 21, 726–731; O'Connel, C. D, Juhasz, A., Kuo, C., Reeder, D. J., Hoon, D. S. B. Clin. Chem. 1998, 44, 1161–1169) The immunoassays are carried out by mixing the sample with haptens or antibodies labeled with an electrochemiluminescent compound and paramagnetic beads coated with complementary antibodies. After allowing time for the antibody reaction to take place, the solution is pumped into a flow cell where material bound to the paramagnetic beads is concentrated on an electrode magnetically. Electrochemiluminescence is initiated by applying a positive potential to the electrode either before or after washing away unbound material. These assays illustrate the advantages of electrochemiluminescence as an analytical technique, including speed, sensitivity, automation and detection over a wide range of concentrations.

Like luminol, acridan compounds can be oxidized enzymatically or electrochemically, and in both cases the oxidation product reacts with $H_2O_2$ to generate chemiluminescence. The detection limits of both compounds were similar under the specific conditions used, and in the concentration range suitable for immunoassays and nucleotide assays. In order to carry out immunoassays or hybridization assays with an acridan compound it is necessary to provide a linking or labeling group for covalent attachment to a marker compound such as an antibody or a nucleic acid probe. Attachment of electrochemiluminescent labeling compounds to analytes and specific binding compounds can be performed by any suitable reaction known generally to those of skill in organic chemistry and assay development.

It is contemplated that intercalation of an acridan into a nucleotide double helix may shield it from oxidation by an electrode in a manner related to the shielding of acridinium ester hydrolysis by intercalation. This would provide an additional assay format. ECL of acridans in matrices where light emission from compounds such as luminol is quenched is also contemplated.

EXAMPLES

2',6'-Difluorophenyl 10-methylacridan-9-carboxylate (DMC) was made by the method disclosed in U.S. Pat. No. 5,593,845. Stock solutions of DMC were prepared in 1:1 ethanol-dioxane. All work was carried out in 10 mM Tris buffer, pH 8.0, containing 0.1 M NaCl, 10 mM, 1 mM EDTA and 0.025% Tween-20 unless otherwise stated. Stock solutions of DMC were dissolved in buffer to give a final solvent concentration of 0.25%. Light was excluded from all DMC solutions.

A second acridan compound 2',3',6'-difluorophenyl 10-methylacridan-9-carboxylate (Lumigen PS-3) was made as described in U.S. Pat. No. 5,593,845. Stock solutions were prepared in 1:1 ethanol: 1,4-dioxane. The acridan phosphate compound 9-(Phenylthiophosphoryloxymethylidene)-10-methyl-acridan, disodium salt (APS-2) was prepared as decribed in U.S. Pat. No. 6,045,727.

Equipment. Transparent electrodes were made from ITO coated glass from Balzer Ltd. (Buckinghamshire, UK) that had a sheet resistance of 200 W/® (ohms per square). Linear sweep measurements were carried out in a three electrode cell made of a cuvette which was placed in a Perkin-Elmer MPF-43 spectrofluorometer. The reference electrode was a silver chloride coated silver wire immersed in the solution under study, and the counter electrode was a platinum wire. These electrodes were located in the cell behind an ITO coated glass working electrode. The ITO surface faced the detector which was set at 430 nm with a slit width of 20 nm. Potentials were controlled with an in-house built potentiostat and a waveform generator (PPR1, Hi-Tek Instruments, Buckinghamshire, England). Cyclic voltammetry was carried out in the same cell, unless otherwise stated, with an Eco Chemie Autolab PGSTAT20 potentiostat (Eco Chemie, Urtrecht, Netherlands). Flow injection measurements were carried out in the thin layer flow cell, with an ITO working electrode and an Ag/AgCl counter/reference electrode. The PMT voltage was 1000 V except for detection limit measurements when the voltage was 1500 V. The laminar flow cell is shown in FIG. 1. The body of this cell was made of PTFE; it was sealed to the ITO working electrode with damp-proof double sided adhesive tape. All potentials are relative to Ag/AgCl.

Electrochemiluminescence of DMC

Linear Sweep Measurements. DMC was dissolved to a final concentration of 50 µM in buffer containing 10 mM $H_2O_2$. Light intensity at 430 nm and current were recorded as the potential was swept in an anodic direction at 10 mV $s^{-1}$.

Real Time ECL Transients. DMC was dissolved to a final concentration of 5 nM in buffer containing 10 mm $H_2O_2$. Transients were obtained by pumping the solution into the thin layer flow cell and recording the light intensity for a total of 180 s: from 0 to 30 s the applied potential was 0 V, from 30 to 60 s it was 1 V and from 60 to 180 s it was 0 V. A second set of transients were obtained in the same way except that the time for which a potential of 1 V was applied was extended to a total of 180 s.

Effect of Hydrogen Peroxide and pH on ECL. The effect of hydrogen peroxide was investigated by dissolving DMC to a final concentration of 10 nM in buffer containing $H_2O_2$ in the concentration range 0 to 50 mM. The effect of pH was investigated by dissolving DMC to a final concentration of 10 nM in buffer containing 10 mM AMP and 10 mM $H_2O_2$ in the pH range 7 to 10. Measurements were made in the thin layer cell by integrating the light intensity for 30 s when the applied potential was 0 V and subtracting it from the integral obtained when the applied potential was 1 V for 30 s. Five measurements were made at each concentration/pH during a total time of 40 minutes.

Stability Measurements. DMC (10 µM), in phosphate buffered saline (PBS) containing 1 mM EDTA and 0.025% Tween-20, was assayed for activity during a total time of 8 hours, by diluting it to a final concentration of 100 nM with TRIS buffer containing 10 mM $H_2O_2$, and measuring the electrochemiluminescence signal as for hydrogen peroxide concentration and pH.

Detection Limits. DMC in the concentration range 0 to 10 nM was added to buffer containing 10 mM $H_2O_2$. Five measurements were made at each concentration in the same way as for the investigation of hydrogen peroxide concentration and pH.

Figure 4:
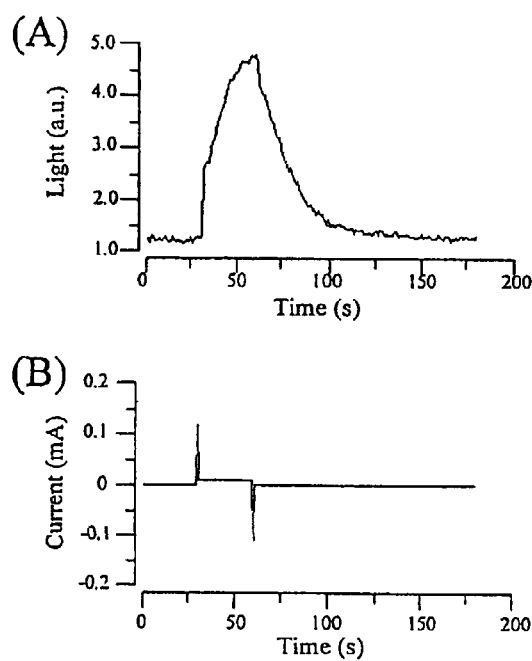
FIG. 4. (A) Light and (B) current transients for a potential step from 0 to 1 V for 5 nM DMC at pH 8.0, in 10 mM Tris buffer with 0.1 M NaCl, 10 mM hydrogen peroxide, 1 mM EDTA and 0.025% Tween-20.
Figure 4:
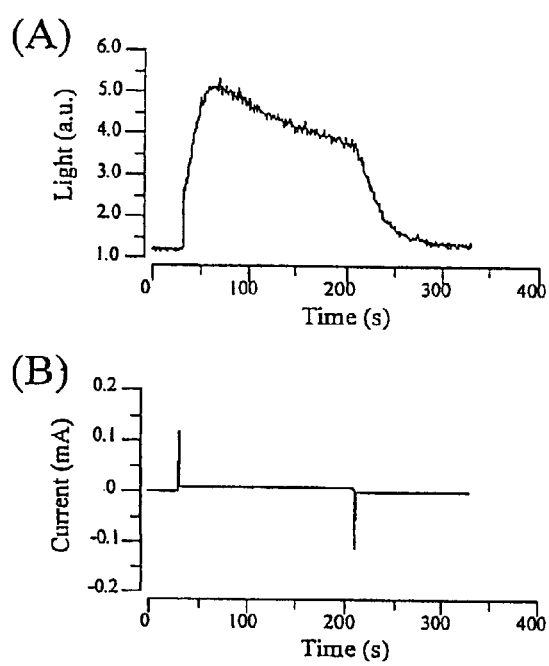

Linear sweep voltammetry showed (FIG. 3) that peak electrochemiluminescence occurred at a potential of 0.75 V, which corresponds to the two electron oxidation of DMC to the acridinium ester followed by chemiluminescence reaction of the acridinium ester with hydrogen peroxide. This implies that a potential in excess of 0.75 V would be suitable for analytical work and the real time transients shown in FIG. 4 record how light intensity varied with time when a potential of 1.0 V was applied to nanomolar concentrations of DMC in the laminar flow cell; most of the current is due to the oxidation of EDTA which has no effect on the light emitting reaction. Pseudo-base does not form because the acridinium ester is produced in the presence of hydrogen peroxide, which immediately reacts with it at a rate which is about $10^4$ times faster than the rate at which hydroxide ions form an adduct.

Electrochemiluminescence of PS-3

Linear Sweep Measurements. PS-3 and luminol were dissolved to a final concentration of 50 µM in buffer 1 containing 10 mM $H_2O_2$. Light intensity and current were recorded as the potential was swept in an anodic direction at 10 mV $s^{-1}$. Solutions. Buffer 1: 10 mM TRIS buffer, pH 8.0, 0.1 M NaCl, 1 mM EDTA 0.025% Tween-20. Buffer 2: 0.15 M phosphate buffer, pH 7.0, 10 mM NaCl, 0.05% Tween-20

Cyclic Voltammetry. Two successive cyclic voltammograms (CVs) of PS-3 (50 µM) in buffer 1 were obtained; EDTA was omitted from the buffer because it is electroactive in the same potential region as PS-3 and obscures its electrochemistry; cyclic voltammetry of PS-3 was repeated in the presence of 10 mM $H_2O_2$. A CV of luminol (50 µM) in buffer 1 was obtained; again EDTA was omitted because it is electroactive.

Real Time ECL Transients. PS-3 and luminol were dissolved to a final concentration of 5 nM in buffer 1 containing 2.5 mM $H_2O_2$ (10 mM for luminol). Transients were obtained by pumping the solution into the thin layer flow cell and recording the light intensity for a total of 180 s: from 0 to 30 s the applied potential was 0 V, from 30 to 210 s it was 1 V, and from 210 to 330 s it was 0 V.

Effect of $H_2O_2$ concentration and pH on ECL of PS-3 and Luminol. The effect of $H_2O_2$ was investigated by dissolving PS-3 or luminol to a final concentration of 10 nM in buffer 1 containing $H_2O_2$ in the concentration range 0 to 10 mM (0 to 50 mM $H_2O_2$ for luminol). The effect of pH in the range 7 to 10 was investigated by dissolving PS-3 or luminol to a final concentration of 10 nM in buffer 1 containing 10 mM 2-amino-2-methyl-1-propanol and 2.5 mM $H_2O_2$ (10 mM $H_2O_2$ for luminol). Measurements were made in the thin layer flow cell by integrating the light intensity for 30 s when the applied potential was 0 V and subtracting it from the integral obtained when the potential was 1 V for 30 s. Five measurements were made at each $H_2O_2$ concentration/pH during a total time of 40 minutes. The effect of $H_2O_2$ concentration and pH on ECL of PS-3 was similar to that on DMC chemiluminescence.

Detection Limits. PS-3 and luminol in the concentration range in 0 to 1250 pM were dissolved in buffer 1 containing 2.5 mM $H_2O_2$ (10 mM $H_2O_2$ for luminol). Measurements were made in the thin layer flow cell as for the effect of $H_2O_2$ and pH on PS-3 and luminol.

Linear Sweep Measurements and Effect of Applied Potential on ITO. The potential dependence of ECL for PS-3, and luminol were examined; the peak potentials are 0.750 V (PS-3) and 0.685 V (luminol). These results suggest that an applied potential of 1 V is suitable for the ECL detection of PS-3 and luminol. Potential cycling experiments supported the conclusion made by other investigators that potentials more anodic than 1V cause irreversible corrosion of ITO electrodes. To avoid this it a maximum potential of 1.0 V was used for all work carried out in the thin layer flow cell.

Electrochemistry and ECL of PS-3. The electrochemistry and ECL of PS-3 is similar to DMC. The results support a process in which electrochemical oxidation of the acridan produces the corresponding acridinium ester, which reacts with $H_2O_2$ resulting in light emission at 430 nm. As was observed for DMC, the CVs show a pattern of three peaks. One peak coincides closely to maximum ECL intensity and corresponds to a net two electron oxidation of the acridan to the acridinium ester. The second and third peaks represent the one electron reduction of the acridinium ester to an acridanyl radical and its re-oxidation to the ester respectively; these peaks do not appear when cyclic voltammetry is carried out in the presence of $H_2O_2$.

Real Time ECL Transients. In ECL transients of PS-3 and luminol, light intensity reaches a maximum a few seconds after the application of a positive potential indicating that the subsequent chemiluminescence reaction is rapid. For the acridan ester the speed of the subsequent reaction is governed by the pKa of the phenolic leaving group, and it is interesting to contrast the more rapid luminescence decay kinetics of PS-3 compared to DMC which has a less efficient leaving group. In solutions where interference from background ECL or electroluminescence is a problem, manipulation of the reaction kinetics could be used to produce a sustained glow that could be integrated after the potential has been returned to zero.

Effect of Hydrogen Peroxide and pH on PS-3 and Luminol ECL. At pH 8.0 PS-3 was stable for an extended time if the $H_2O_2$ concentrations did not exceed 2.5 mM; this instability increased with increasing pH. Further investigation showed that PS-3 was stable at pH 9.0 for at least 40 minutes in the absence of $H_2O_2$, and that dissolved oxygen did not accelerate the rate of inactivation observed in the presence of $H_2O_2$. Further work on PS-3 was carried out at pH 8.0 and a $H_2O_2$ concentration of 2.5 mM where it was stable for at least 40 minutes.

Detection Limits. Plots of integrated light intensity against the concentration of PS-3 were linear in the concentration range 0 to 1250 pM. The limits of detection (2×S.D. Blank (n=9)) were 67 pM for PS-3 and 72 pM for luminol. In both cases the plot of integrated light intensity against concentration did not pass through the origin at zero concentration because of the background electroluminescence that accompanies $H_2O_2$ oxidation on ITO electrodes.

Electrochemiluminescence of an Acridan Phosphate

The acridan phosphate compound designated APS-2:

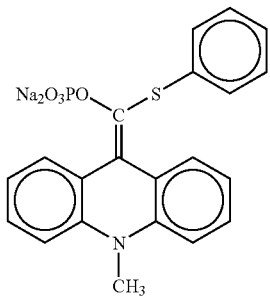

was found to exhibit electrochemiluminescence under oxidative conditions under the coditions described above using PS-3. APS-2 was dissolved to a final concentration of 50 μM in buffer 1 containing 10 mM $H_2O_2$. Light intensity and current were recorded as the potential was swept in an anodic direction at 10 mV s$^{-1}$. Buffer 1: 10 mM TRIS buffer, pH 8.0, 0.1 M NaCl, 1 mM EDTA 0.025% Tween-20. Buffer 2: 0.15 M phosphate buffer, pH 7.0, 10 mM NaCl, 0.05% Tween-20

Cyclic Voltammetry. Two successive cyclic voltammograms (CVs) of APS-2 (50 μM) in buffer 1 were obtained in the presence of 10 mM $H_2O_2$; EDTA was omitted from the buffer because it is electroactive in the same potential region as APS-2 and obscures its electrochemistry. Cyclic voltammetry of APS-2 in the absence of $H_2O_2$ produced no light.

What is claimed is:

1. A method for producing electrochemiluminescence comprising:
   a) providing a solution of an acridan compound and a peroxide, wherein the acridan compound has the formula

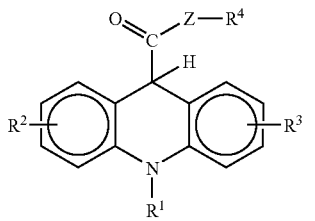

wherein $R^1$ to $R^4$ are independently selected from hydrogen and organic groups containing from 1 to 50 non-hydrogen atoms selected from C, N, O, S, P and halogen atoms, Z is selected from O, S and $NR^5$, $R^5$ is selected from substituted or unsubstituted alkyl, substituted or unsubstituted aryl, alkylsulfonyl and arylsulfonyl groups; and
   b) electrochemically oxidizing the acridan compound at a electrode to form an oxidized intermediate compound wherein the oxidized intermediate compound reacts with the peroxide provided in the solution to produce the chemiluminescence.

2. The method of claim 1 wherein $R^1$ to $R^4$ are selected from alkyl, aryl, alkenyl, alkynyl or aralkyl any of which can be substituted, halogen, hydroxy, alkoxy, amino, alkylamino, carbonyl-containing groups such as keto, carboxy, carboxamide and carboalkoxy, thio, alkylthio, cyano, nitro, trialkyl-silyloxy, alkylsulfonyl, arylsulfonyl, and positively or negatively charged ionic groups which improve water solubility.

3. The method of claim 1 wherein the acridan compound serves as an electrochemiluminescent labeling compound and wherein at least one of the groups $R^1$–$R^4$ in the acridan compound is a labeling substituent of the formula

-L-RG wherein L is a linking group which can be a bond or another divalent or polyvalent group, RG is a reactive group which enables the acridan compound to be bound to another compound.

4. The method of claim 3 wherein L is selected from a bond, an atom, a straight chain group, a branched chain group or a ring group wherein the chain or ring group contains from 2 to about 50 non-hydrogen atoms selected from C, O, N, S, P, Si, B, and Se atoms, and can be substituted with halogen atoms on the chain or ring.

5. The method of claim 3 wherein L is selected from alkylene, arylene, alkenylene, ether, peroxide, ketone, ester, carbonate ester, thioester, amide, amine, amidine, carbamate, urea, imine, imide, imidate, carbodiimide, hydrazine, diazo, phosphodiester, phosphotriester, phosphonate ester, thioether, disulfide, sulfoxide, sulfone, sulfonate ester, sulfate ester, and thiourea groups.

6. The method of claim 3 wherein RG is selected from halogen atom or a tosylate group, isocyanate or isothiocyanate group, a maleimide group, a group which can react by a Michael addition reaction and a group which can react by a nucleophilic displacement reaction.

7. The method of claim 1 wherein the acridan compound is selected from

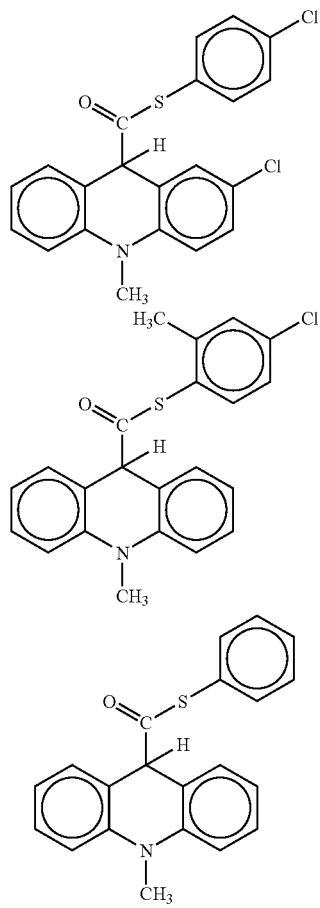

-continued
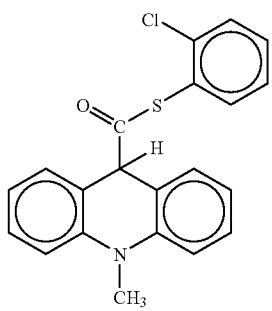
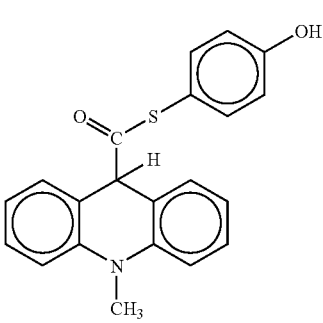
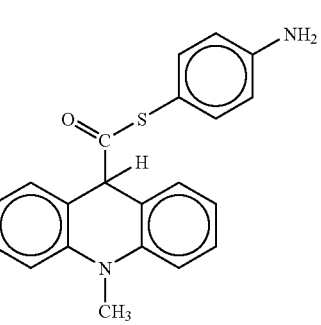
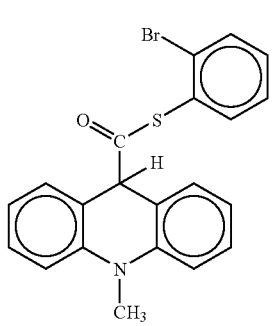
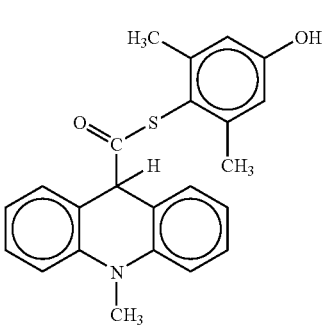
-continued
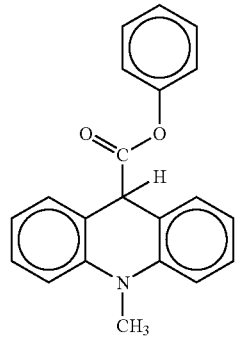
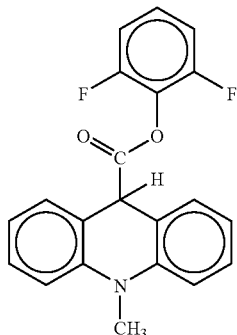
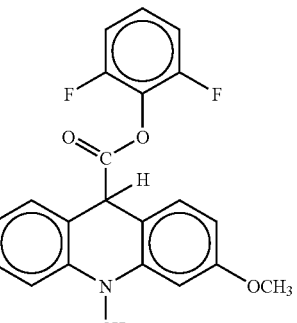
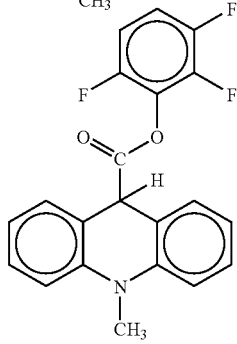
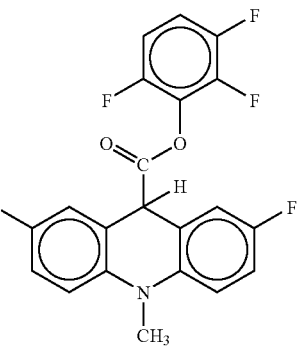

-continued

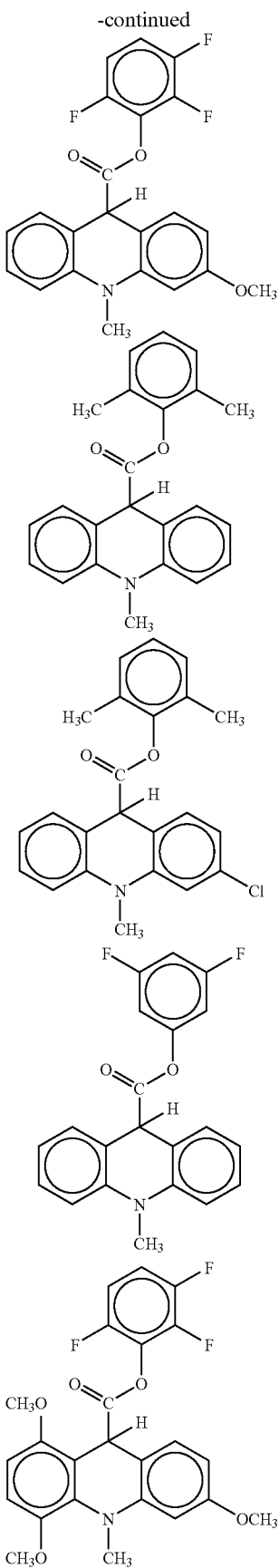

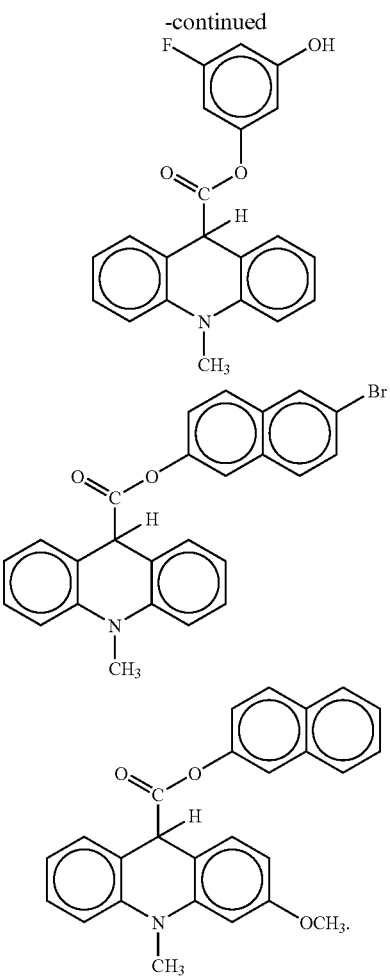

8. A method for producing electrochemiluminescence comprising:

a) providing a solution of an acridan compound and a peroxide, wherein the acridan compound has the formula:

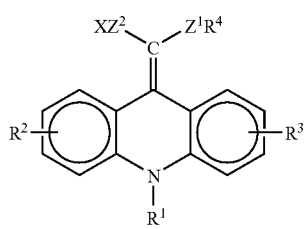

wherein $R^1$ to $R^4$ are independently selected from O, S and $NR^5$, $R^5$ is selected from substituted or unsubstituted alkyl, substituted or unsubstituted aryl, alkylsulfonyl and arylsulfonyl groups, $R^1$ to $R^4$ are independently selected from hydrogen and organic groups containing from 1 to 50 non-hydrogen atoms selected from C, N, O, S, P and halogen atoms, and X is selected from hydrogen and organic groups containing from 1 to 50 non-hydrogen atoms selected from C, N, O, S, P and halogen atoms;

b) electrochemically oxidizing the acridan compound at a electrode to form an oxidized intermediate compound wherein the oxidized intermediate compound reacts with the peroxide provided in the solution to produce the chemiluminescence.

9. The method of claim 8 wherein $R^1$ to $R^4$ are selected from alkyl, aryl, alkenyl, alkynyl or aralkyl any of which can be substituted, halogen, hydroxy, alkoxy, amino, alkylamino, carbonyl-containing groups such as keto, carboxy, carboxamide and carboalkoxy, thio, alkylthio, cyano, nitro, trialkyl-silyloxy, alkylsulfonyl, arylsulfonyl, and positively or negatively charged ionic groups which improve water solubility.

10. The method of claim 8 wherein X is selected from an alkyl, aryl, aralkyl, alkenyl or alkynyl group of 1–20 carbon atoms any of which can be substituted, or is selected from substituted or unsubstituted alkyl or aryl carbonyl groups having from 1–20 carbon atoms, tri($C_1$–$C_8$ alkyl)silyl groups, an $SO_3^-$ group, glycosyl groups and phosphoryl groups of the formula PO(OR')(OR") wherein R' and R" are independently selected from substituted or unsubstituted alkyl, substituted or unsubstituted aryl and substituted or unsubstituted aralkyl groups of 1–20 carbon atoms, trialkylsilyl groups, alkali metal cations, alkaline earth cations, ammonium and phosphonium cations.

11. The method of claim 8 wherein the acridan compound serves as an electrochemiluminescent labeling compound and wherein at least one of the groups $R^1$–$R^4$ in the acridan compound is a labeling substituent of the formula

-L-RG wherein L is a linking group which can be a bond or another divalent or polyvalent group, RG is a reactive group which enables the acridan compound to be bound to another compound.

12. The method of claim 11 wherein L is selected from a bond, an atom, a straight chain group, a branched chain group or a ring group wherein the chain or ring group contains from 2 to about 50 non-hydrogen atoms selected from C, O, N, S, P, Si, B, and Se atoms, and can be substituted with halogen atoms on the chain or ring.

13. The method of claim 11 wherein L is selected from alkylene, arylene, alkenylene, ether, peroxide, ketone, ester, carbonate ester, thioester, amide, amine, amidine, carbamate, urea, imine, imide, imidate, carbodiimide, hydrazine, diazo, phosphodiester, phosphotriester, phosphonate ester, thioether, disulfide, sulfoxide, sulfone, sulfonate ester, sulfate ester, and thiourea groups.

14. The method of claim 11 wherein RG is selected from halogen atom or a tosylate group, isocyanate or isothiocyanate group, a maleimide group, a group which can react by a Michael addition reaction and a group which can react by a nucleophilic displacement reaction.

15. The method of claim 8 wherein the acridan compound has the formula:

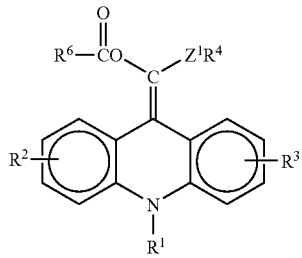

wherein M is a cation selected from an alkali metal ion or an ammonium, quaternary ammonium or quaternary phosphonium ion.

16. The method of claim 8 wherein the acridan compound has the formula:

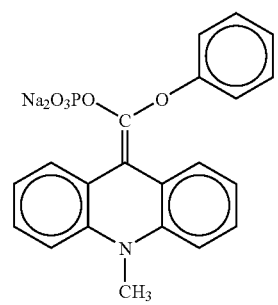

wherein $R^6$ is an alkyl or aryl group which can be further substituted.

17. The method of claim 8 wherein the acridan compound is selected from

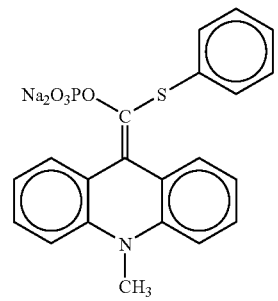

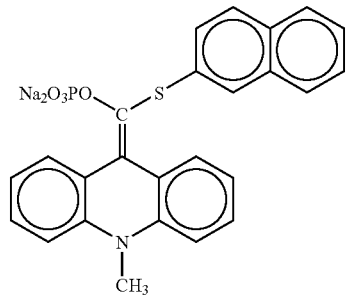

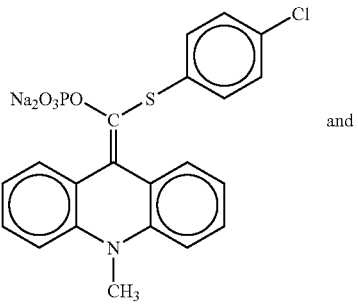

and

-continued

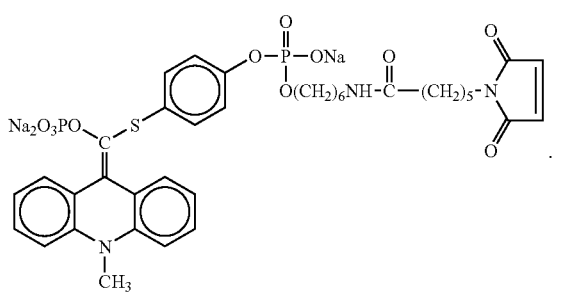

18. The method of claim 1 or claim 8 wherein the peroxide is hydrogen peroxide.

19. The method of claim 1 or claim 8 wherein the electrochemical oxidation of the acridan compound is conducted at a positive potential relative to a Ag/AgCl electrode.

20. The method of claim 1 or claim 8 wherein the electrode at which the electrochemical oxidation is performed is selected from a graphite rod, platinum wire, a platinum mesh or a transparent indium tin oxide electrode.

21. The method of claim 1 or claim 8 wherein electrochemiluminescence is produced by sweeping a voltage at the anode of an electrochemical cell to a first, positive potential and then reversing the voltage to a second, lower potential to extinguish electrochemiluminescence.

22. The method of claim 1 or claim 8 wherein the acridan compound is provided as a label on a marker compound selected from a hapten, an antibody or a nucleic acid probe.

* * * * *